(12) United States Patent
Van Eert et al.

(10) Patent No.: US 8,048,997 B2
(45) Date of Patent: Nov. 1, 2011

(54) PROCESS FOR DRYING URONIC ACID OLIGOSACCHARIDES

(75) Inventors: Martin Van Eert, Zoetermeer (NL); Bernd Stahl, Rosbach (DE); Antonie Van Baalen, Arnhem (NL)

(73) Assignee: N.V. Nutricia, Zoetermeer (NL)

( * ) Notice: Subject to any disclaimer, the term of this patent is extended or adjusted under 35 U.S.C. 154(b) by 755 days.

(21) Appl. No.: 11/912,097

(22) PCT Filed: Apr. 21, 2006

(86) PCT No.: PCT/NL2006/050095
§ 371 (c)(1),
(2), (4) Date: Nov. 12, 2007

(87) PCT Pub. No.: WO2006/112718
PCT Pub. Date: Oct. 26, 2006

(65) Prior Publication Data
US 2008/0193627 A1 Aug. 14, 2008

(30) Foreign Application Priority Data
Apr. 22, 2005 (EP) .................... 05103302

(51) Int. Cl.
*A61K 31/732* (2006.01)
*A61K 31/715* (2006.01)
*A61K 31/702* (2006.01)
*C08B 37/06* (2006.01)
*C07H 1/00* (2006.01)

(52) U.S. Cl. ............ 536/2; 536/123.1; 536/123.13; 514/53; 514/54; 514/61

(58) Field of Classification Search ............ None
See application file for complete search history.

(56) References Cited

U.S. PATENT DOCUMENTS

| | | | |
|---|---|---|---|
| 3,920,815 A * | 11/1975 | Harvey et al. | 514/8 |
| 4,529,613 A | 7/1985 | Mezzino et al. | |
| 5,039,543 A * | 8/1991 | Lee et al. | 426/533 |
| 5,498,702 A * | 3/1996 | Mitchell et al. | 536/2 |
| 5,738,805 A | 4/1998 | Chaundy et al. | |
| 6,482,806 B1 * | 11/2002 | Koyama et al. | 514/54 |
| 6,663,717 B2 * | 12/2003 | Antila et al. | 127/34 |
| 2003/0022863 A1 | 1/2003 | Stahl et al. | |

FOREIGN PATENT DOCUMENTS

| | | |
|---|---|---|
| EP | 0 824 872 A | 2/1998 |
| EP | 0824872 * | 2/1998 |
| EP | 0 868 854 A | 10/1998 |
| EP | 0 888 776 A | 1/1999 |
| EP | 1 206 909 A | 5/2002 |
| GB | 1 515 961 A | 6/1978 |
| WO | WO 02/42484 A | 5/2002 |

OTHER PUBLICATIONS

Merriam-Webster's Collegiate Dictionary, Tenth Edition, published 1998 by Merriam-Webster, Incroprorated, p. 924.*

Voragen et al., "Non-enzymatic browning of oligogalacturonides in apple juice models" Z. Lebensm Unters Forsch. (1988) vol. 187 pp. 315-320.*

* cited by examiner

*Primary Examiner* — Eric S Olson

(74) *Attorney, Agent, or Firm* — Gilberto M. Villacorta; Sunit Talapatra; Foley & Lardner LLP

(57) ABSTRACT

The present invention relates to a process for spray drying uronic acid oligosaccharides and to a powder compositions thus obtained. Typically the powder composition comprises between 25 and 100 wt.% uronic acid oligosaccharide with a DP between 2 and 50 based on total weight of uronic acid, with and an average particle size between 20 μm and 100 μm.

7 Claims, 1 Drawing Sheet

PROCESS FOR DRYING URONIC ACID OLIGOSACCHARIDES

This is a U.S. national phase entry of PCT/NL2006/050095, filed on Apr. 22, 2006, which claims priority from EP 05103302.5, filed on Apr. 22, 2005, the disclosure of which are incorporated herein in their entirety by reference.

FIELD OF THE INVENTION

The present invention relates to a process for spray drying uronic acid oligosaccharides.

BACKGROUND OF THE INVENTION

Hydrolysis products of viscous soluble fibers are described to have beneficial effects, e.g. diarrhea preventive and preventing the adherence of pathogenic microorganisms to the epithelial cells of the gastrointestinal tract, see for example EP1267891.

However, despite these advantageous uses of the hydrolysis products of viscous fibers, particularly of pectin, they are generally not in found in commercial products aimed for oral ingestion by humans. WO 02/42484 describes a method for producing pectin hydrolysis products and the use thereof.

Before using hydrolysis products of uronic acid polymers, several (potential) difficulties have to be overcome. For example, uronic acid oligosaccharides are difficult to handle, i.e. they are produced in aqueous solutions with low dry matter content, and hence prone to bacterial contamination and thus difficult to store. Additionally, the oligosaccharides are prone to maillardation, particularly when brought into contact with other carbohydrates and protein, potentially resulting in undesirable Maillard reaction products with concomitant undesirable effects on color, odor and taste of the product.

Because of the presumed difficulties attached to their use, the oligosaccharides are not or only very limitedly used in food applications. If used, the food processing step will be designed so that contact between the uronic acid oligosaccharides and the other components is avoided in a reactive environment, e.g. by dry blending the uronic acid oligosaccharides. Dry blending has additional disadvantages, because it is expensive and often results in size or density separation of the particles during transport, yielding unacceptable products.

SUMMARY OF THE INVENTION

The present inventors have found that spray drying aqueous products containing the uronic acid oligosaccharides, with a DP between 2 and 250 yields highly beneficial powders, which can be suitably used for food applications.

Hence, in one aspect, is was found that aqueous compositions which contain a relatively low dry matter content with a high weight percentage of uronic acid oligosaccharides can be suitably spray dried, yielding powdered products which can suitably be used for further processing in food products. It was found that the process does not require the addition of significant amounts of carrier material.

In a further aspect, it was found that an aqueous solution containing uronic acid oligosaccharides, carbohydrates and protein can be spray dried without unacceptable Maillard reactions occurring, and hence yielding a product with highly advantageous properties and which is ready for use in food products.

The particles of the powdered products contain, besides uronic acid oligosaccharide also other nutritional macronutrients such as protein and carbohydrates. The combined spray drying of acid oligosaccharides and macronutrients ensures a more constant nutritional profile per portion obtained from the powder bulk and thus overcomes the problems such as size and/or density separation of powder particles. A constant nutritional profile of individual portions is of particular importance when manufacturing infant nutrition. Hence, in one aspect the present invention relates to a powdered product, with the nutritional profile of an infant nutrition.

In still a further aspect, it was found that an aqueous solution containing uronic acid oligosaccharides and soluble dietary fibers, particularly indigestible fermentable oligosaccharides, can be spray dried without significant Maillard reactions occurring, even when in combination with protein.

The present invention also provides a composition obtainable by the process described herein. Due to the spray drying process, the oligosaccharides in the product are now better distributed over the powder compared to a situation where powdered oligosaccharides are dry blended into an infant nutrition. The individual particles in the powder composition resulting from spray drying contain a combination comprising uronic acid oligosaccharides and macronutrients. Conventional mixing techniques e.g. dry blending, results in a powder mixture of separate particles.

Furthermore, pectin and seaweed polymers are normally roller dried or drum dried which yield a powder product with undesirable properties and characteristics. The spray dried powders of the present invention, containing high concentrations of oligosaccharides, can be distinguished from those prepared by roller or drum drying by their particle size, e.g. the spray dried particles have a median particle size of 20 to 100 μm, preferably between 30 and 80 μm. Roller-dried powder particles, have normally a median particle size of about 150 μm.

DETAILED DESCRIPTION OF PREFERRED EMBODIMENTS

Figure 1:
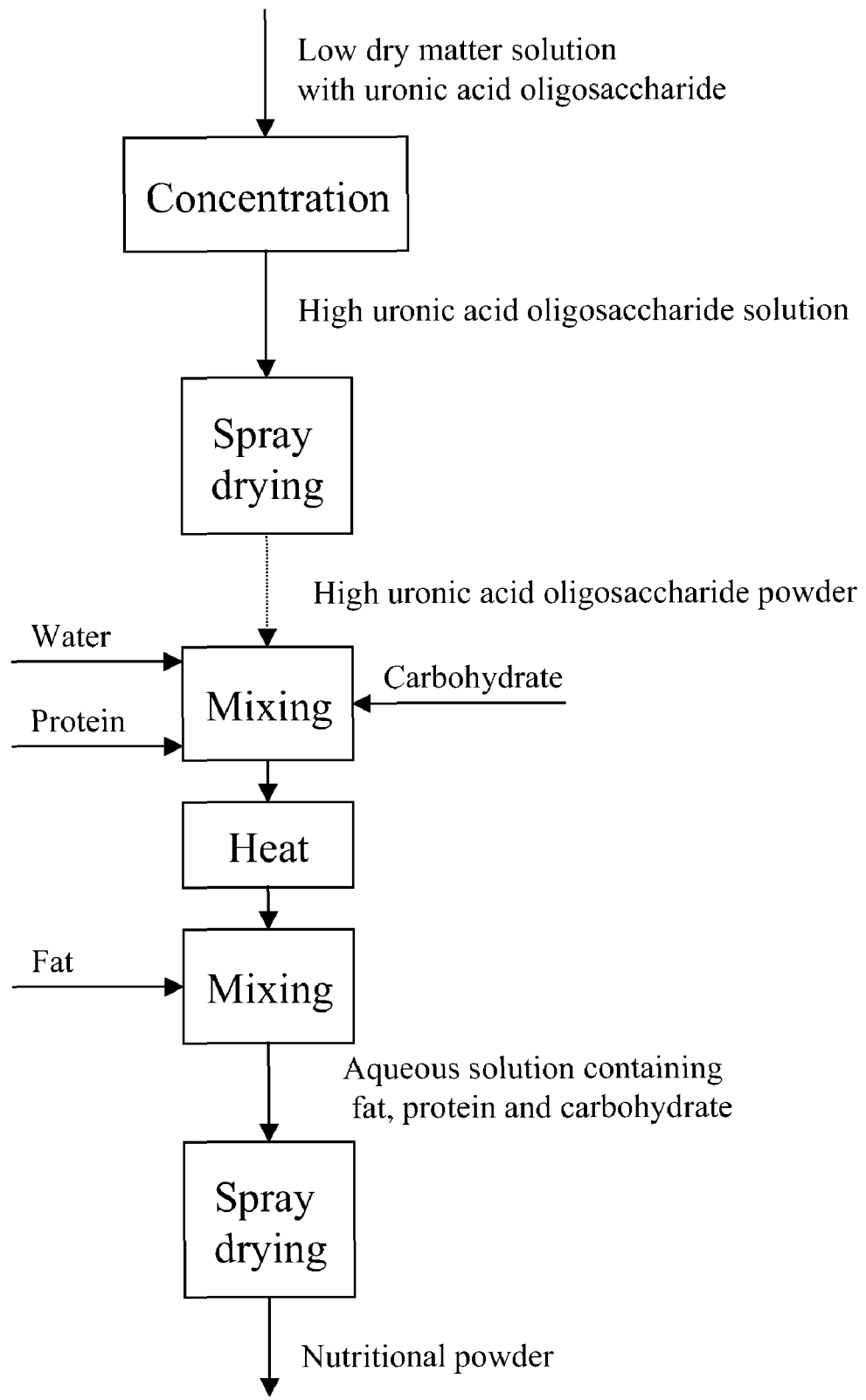
FIG. 1 shows a schematic representation of a preferred process for drying uronic acid oligosaccharides.

In one aspect the present invention provides a process for the manufacture of a powder from an aqueous solution comprising a spray drying step wherein said aqueous composition is spray dried to form a powder, characterized in that the aqueous solution comprises between 25 and 100 wt. % uronic acid oligosaccharide with a DP of 2 to 250 based on total weight of uronic acid; at least 0.1 grams uronic acid per liter; and a dry matter content between 10 and 80 wt. % based on the total weight of the aqueous solution.

In a further aspect the present invention provides a powder obtainable by the present process.

In still a further aspect, the present invention provides a powder composition containing between 25 and 100 wt. % uronic acid oligosaccharide with a DP between 2 and 50 based on total weight of uronic acid, said powder composition having an average particle size between 20 μm and 100 μm.

The present invention also provides an aqueous solution comprising between 2 and 25 g protein per 100 grams dry weight, between 20 and 80 digestible carbohydrate per 100 grams dry weight and between 0.05 and 5 wt. % uronic acid oligosaccharide based on dry weight of the aqueous solution. The dry weight of a composition is typically the weight that remains when the water is evaporated.

In a further aspect the present invention provides a food product comprising a powder composition according to the present invention or an aqueous solution according to the present invention.

Uronic Acid Oligosaccharides

The term uronic acid oligosaccharide as used in the present invention refers to a oligosaccharide wherein preferably at least 50% of the residues are selected from the group consisting of guluronic acid, mannuronic acid, galacturonic acid and glucuronic acid. In a preferred embodiment the uronic acid oligosaccharide contains at least 50% galacturonic acid based on total uronic acid residues in the acid oligosaccharide. More preferably, the present uronic acid oligosaccharide is a polygalaturonic acid oligosaccharide (also referred to as galacturonic acid oligosaccharide), preferably hydrolysed pectin. The galactoronic acid oligosaccharides are preferably obtainable by enzymatic digestion of pectin with pectin lysase, pectic lyase, endopolygalacturonase and/or pectinase. The galacturonic acid oligosaccharide may be methoxylated and/or amidated.

The uronic acid oligosaccharide is preferably indigestible in the upper human intestinal tract and water-soluble. The uronic acid oligosaccharides are preferably prepared by hydrolysis of pectin, e.g. apple, citrus or sugar beet pectin.

Preferably the uronic acid oligosaccharide has a degree of polymerization (DP) between 2 and 250, preferably between 2 and 50, even more preferably between 2 and 10. If a mixture of uronic acid oligosaccharides with different DP's are used, the average DP is preferably between 2 and 250, more preferably between 2 and 50, even more preferably between 2 and 10. Preferably the galacturonic acid oligosaccharide has a degree of polymerization (DP) between 2 and 250, preferably between 2 and 50, even more preferably between 2 and 10. If a mixture of galacturonic acid oligosaccharides with different DP's are used, the average DP is preferably between 2 and 250, more preferably between 2 and 50, even more preferably between 2 and 10.

In a preferred embodiment, the present composition contains between 25 and 100 wt. % uronic oligosaccharides with a DP between 2 and 250 based on total weight of uronic acid, more preferably between 50 and 100 wt. %, even more preferably between 75 and 100 wt. %. More preferably, the present composition contains between 25 and 100 wt. % uronic oligosaccharides with a DP between 2 and 50 based on total weight of uronic acid, more preferably between 50 and 100 wt. %, even more preferably between 75 and 100 wt. %. The uronic acid oligosaccharide is preferably indigestible in the upper human intestinal tract and water soluble.

In a preferred embodiment, the present composition contains between 25 and 100 wt. % galacturonic oligosaccharides with a DP between 2 and 250 based on total weight of galacturonic acid, more preferably between 50 and 100 wt. %, even more preferably between 75 and 100 wt. %. More preferably, the present composition contain between 25 and 100 wt. % galacturonic oligosaccharides with a DP between 2 and 50 based on total weight of galacturonic acid, more preferably between 50 and 100 wt. %, even more preferably between 75 and 100 wt. %. The galacturonic acid oligosaccharide is preferably indigestible in the upper human intestinal tract and water soluble.

In a preferred embodiment, at least one of the terminal hexuronic units of the uronic acid oligosaccharide has a double bond, which is preferably situated between the $C_4$ and $C_5$ position of the terminal hexuronic unit. Preferably one of the terminal hexuronic units comprises the double bond. The terminal hexuronic (e.g. uronic acid) preferably has a structure according to the FIGURE below.

Preferred terminal hexuronic acid group

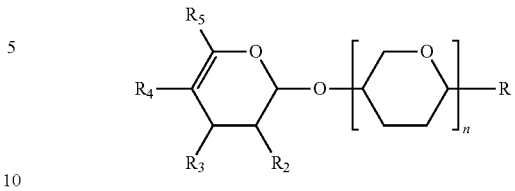

wherein;

R is preferably selected from the group consisting of hydrogen, hydroxy or acid group, preferably hydroxy (see above); and at least one selected from the group consisting of $R_2$, $R_3$, $R_4$ and $R_5$ represents N-acetylneuraminic acid, N-glycoloyl-neuraminic acid, free or esterified carboxylic acid, sulfuric acid group or phosphoric acid group, and the remaining of $R_2$, $R_3$, $R_4$ and $R_5$ representing hydroxy and/or hydrogen. Preferably one selected from the group consisting of $R_2$, $R_3$, $R_4$ and $R_5$ represents free or esterified carboxylic acid, sulfuric acid group or phosphoric acid group, and the remaining of $R_2$, $R_3$, $R_4$ and $R_5$ represent hydroxy and/or hydrogen. Even more preferably one selected from the group consisting of $R_2$, $R_3$, $R_4$ and $R_5$ represents free or esterified carboxylic acid and the remaining of $R_2$, $R_3$, $R_4$ and $R_5$ represent hydroxy and/or hydrogen; and n is an integer and refers to a number of hexuronic units, which may be any hexuronic unit. Suitably n is an integer between 1-49 representing the number of hexuronic units said hexuronic units preferably being uronic acid, even more preferably being galacturonic acid units. The carboxylic acid groups on these units may be free or (partly) esterified, and are preferably at least partly methylated.

Most preferably, $R_2$ and $R_3$ represent hydroxy, $R_4$ represent hydrogen and $R_5$ represents free or esterified carboxylic acid.

In a further embodiment, a mixture of uronic acid oligosaccharides (e.g. pectin hydrolysate) is used, which have a different DP and/or comprise both unsaturated and saturated terminal hexose unit. Preferably at least 5%, more preferably at least 10%, even more preferably at least 25% of the terminal hexose units of the uronic acid oligosaccharide unsaturated hexose unit (see the FIGURE above). As each individual uronic acid oligosaccharide preferably comprises only one unsaturated terminal hexose unit, preferably no more than 50% of the terminal hexose units is an unsaturated hexose unit (i.e. comprises a double bond).

A mixture of uronic acid oligosaccharides preferably contains between 2 and 50% unsaturated hexose units based on the total amount of hexose units, preferably between 10 and 40%.

The uronic acid oligosaccharides are in one embodiment characterized by a degree of methoxylation above 20%, preferably above 50% even more preferably above 70%. In another embodiment the uronic acid oligosaccharides have a degree of methylation above 20%, preferably above 50% even more preferably above 70%.

Aqueous Solution

The aqueous solution as used in the present process contains between 25 and 100 wt. % uronic acid oligosaccharide with a degree of polymerization (DP) between 2 and 250 based on total weight of uronic acid in the aqueous solution, more preferably between 50 and 100 wt. %, even more preferably between 75 and 100 wt. %. Preferably the aqueous solution contains between 25 and 100 wt. % uronic acid oligosaccharide with a DP between 2 and 50 based on total weight of uronic acid in the aqueous solution, more preferably between 50 and 100 wt. %, even more preferably between 75 and 100 wt. %. Preferably the aqueous solution contains between 25 and 100 wt. % uronic acid oligosaccharide with a DP between 2 and 10 based on total weight of uronic acid in the aqueous solution, more preferably between 50 and 100 wt. %, even more preferably between 75 and 100 wt. %.

The aqueous solution as used in the present process contains between 25 and 100 wt. % galacturonic acid oligosaccharide with a DP between 2 and 250 based on total weight of galacturonic acid in the aqueous solution, more preferably between 50 and 100 wt. %, even more preferably between 75 and 100 wt. %. Preferably the aqueous solution contains between 25 and 100 wt. % galacturonic acid oligosaccharide with a DP between 2 and 50 based on total weight of uronic acid in the aqueous solution, more preferably between 50 and 100 wt. %, even more preferably between 75 and 100 wt. %. Preferably the aqueous solution contains between 25 and 100 wt. % galacturonic acid oligosaccharide with a DP between 2 and 10 based on total weight of galacturonic acid in the aqueous solution, more preferably between 50 and 100 wt. %, even more preferably between 75 and 100 wt. %.

Hence, the aqueous solution and powder products obtained by the present process preferably have a relatively low content of long-chain uronic acid saccharides, e.g. pectin or alginate. A higher wt. % of short chain uronic acid oligosaccharides requires the incorporation of less oligosaccharides in total and reduces possible Maillard reactions and/or viscosity. The average DP of the uronic acid oligosaccharides used in the present invention is preferably between 2 and 50, more preferably between 2 and 10.

In one preferred embodiment the aqueous solution contains at least 50 wt. % uronic acid oligosaccharides based on total dry weight of the aqueous solution, preferably at least 75 wt. %, more preferably at least 90 wt. %. Aqueous solutions containing 50 wt. % or more of the present uronic acid oligosaccharides based on total dry weight of the aqueous solution, are hereinafter referred to as "high uronic acid oligosaccharide solution". The high uronic acid oligosaccharide solution preferably has a dry matter content between 35 and 65 wt. %, even more preferably between 40 and 60 wt. %.

Preferably the high uronic acid oligosaccharide solution has a protein content below 5 wt. % based on dry weight of the high uronic acid oligosaccharide solution, preferably below 1 wt. %. Preferably the high uronic acid oligosaccharide solution has a lipid content below 5 wt. % based on dry weight of the high uronic acid oligosaccharide solution, preferably below 1 wt. %. An increased purity of the high uronic acid oligosaccharide solution yields a more pure uronic acid oligosaccharide containing powder, which can be used over a wider range applications, and is particularly suitable for application in a process for the manufacture of infant formula due to a less complicated quality control process.

In a further preferred embodiment the present invention provides an aqueous solution comprising between 2 and 25 g protein per 100 grams dry weight, between 20 and 80 digestible carbohydrate per 100 grams dry weight and between 0.05 and 5 wt. % uronic acid oligosaccharide based on dry weight of the aqueous solution (hereinafter referred to as "low uronic acid oligosaccharide solution"). This low uronic acid oligosaccharide solution can be suitably spray dried to yield a nutritional powder (e.g. infant nutrition) according to the present invention, e.g. with a uniform distribution of nutritional components and uronic acid oligosaccharides over the particles. The low uronic acid oligosaccharide solution preferably contains between 0.1 and 2 wt. %, even more preferably between 0.25 and 1.25 wt. % of the uronic acid oligosaccharide. The uronic acid oligosaccharide preferably is a galacturonic acid oligosaccharide.

Preferably the aqueous solution comprises fat, protein and carbohydrate, more preferably between 2 and 25 grams protein per 100 grams dry weight, between 20 and 80 grams digestible carbohydrate per 100 grams dry weight, and between 5 and 40 grams fat per 100 grams dry weight. The dietary fiber content of this aqueous solution is preferably between 0.5 and 10 grams per liter. The aqueous solution preferably has a dry matter content of between 20 and 70 wt. % based on total weight of the aqueous solution, more preferably between 40 and 65 wt. %

The Powder

Spray drying the present high uronic acid oligosaccharide solution yields a powder that can be advantageously used in industry, e.g. the powder can be stored for a long time and can be used in food products. The present invention provides a powder composition containing between 25 and 100 wt. % uronic acid oligosaccharide with a DP of 2 to 250 based on total weight of uronic acid in the powder, with an average particle size between 20 µm and 100 µm, preferably between 40 µm and 70 µm. Preferably the powder contains between 25 and 100 wt. % uronic acid oligosaccharide with a degree of polymerization (DP) between 2 and 50 based on total weight of uronic acid, more preferably at least 50 wt. %, even more preferably at least 75 wt. %, most preferably at least 90 wt. %. Preferably the powder contains between 25 and 100 wt. % uronic acid oligosaccharide with a degree of polymerization (DP) between 2 and 10 based on total weight of uronic acid, more preferably at least 50 wt. %, even more preferably at least 75 wt. %, most preferably at least 90 wt. %. Even more preferably the powder contains between 25 and 100 wt. % galacturonic acid oligosaccharide with a degree of polymerization (DP) between 2 and 50 based on total weight of galacturonic acid, more preferably at least 50 wt. %, even more preferably at least 75 wt. %, most preferably at least 90 wt. %. The powder composition preferably has a water content below 8 wt. % based on total weight of the powder, more preferably between 5 and 1 wt. %. This water content ensures an acceptable shelf life.

Spray drying the present high uronic acid oligosaccharide solution yields a powder that contains a high uronic acid oligosaccharide content (hereinafter also referred to as high uronic acid oligosaccharide powder). Hence in a preferred embodiment the present powder comprises at least 50 wt. % of the uronic acid oligosaccharides with a DP of 2 to 250 based on total dry weight of the powder, preferably at least 75 wt. %, even more preferably at least 90 wt. %. More preferably the present powder comprises at least 50 wt. % of the uronic acid oligosaccharides with a DP of 2 to 50 based on total dry weight of the powder, preferably at least 75 wt. %, even more preferably at least 90 wt. %. The high uronic acid oligosaccharide powder has an average particle size between 20 µm and 100 µm, preferably between 40 µm and 70 µm. Preferably at least 50% of the particles in the present uronic acid containing powder have a particle diameter between 20 and 100 µm.

Spray drying the aqueous solution containing the uronic acid oligosaccharide, fat, protein and carbohydrate yields a composition that can be suitably used for nutritional purposes. Preferably this nutritional powder contains fat, protein and carbohydrate and between 0.05 and 5 wt. % uronic acid oligosaccharide with a DP of 2 to 250, more preferably 0.05 to 5 wt. % uronic acid oligosaccharide with a DP of 2 to 50, even more preferably 0.05 to 5 wt. % uronic acid oligosaccharide with a DP of 2 to 10. More preferably this powder contains between 0.2 and 5 wt. % uronic acid oligosaccharide with a DP of 2 to 50, more preferably 0.2 to 5 wt. % uronic acid oligosaccharide with a DP of 2 to 10. The power preferably comprises between 2 and 25 grams protein per 100 grams powder, between 20 and 80 grams digestible carbohydrate per 100 grams powder, and between 5 and 40 grams fat per 100 grams powder. The term protein as used herein includes amino acids, protein hydrolysates and native proteins. More preferably the power comprises between 2 and 25 grams protein per 100 grams powder, between 20 and 80 grams digestible carbohydrate per 100 grams powder, and between 5 and 40 grams fat per 100 grams powder. Preferably the powder contains at least 50 wt. % lactose based on the total weight of the digestible carbohydrate. This powder has a particle size distribution with a single peak in, e.g. the particle size distribution a typical Gaussian curve. This in contrast to the powders where uronic acid oligosaccharides obtained by roller-drying are dry blended to a nutritional powder; such mixtures do not have a uniform particle size distribution, e.g. these mixtures have two peaks in the particle size distribution. Preferably at least 5 wt. % of the present nutritional powder are particles that contain a mixture of protein, fat, carbohydrate and the uronic acid oligosaccharide. The nutritional powder preferably has an average particle size (=particle diameter) between 20 μm and 100 μm, preferably between 40 μm and 70 μm. Preferably at least 50% of the particles in the present uronic acid containing powder have a particle diameter between 20 and 100 μm.

Spray Drying

The present invention provides a process for the production of powdered product from an aqueous solution as described hereinabove, comprising a spray drying step wherein the aqueous composition is spray dried to form a powder.

The spray drying (i.e. drying by spraying) as used herein comprises the process for transforming a solid dissolved or suspended in a liquid into a powdery, possibly agglomerated material. Spray drying typically involves atomization of a liquid feedstock into a spray of droplets and contacting the droplets with hot air in a drying chamber. The sprays are preferably produced by either rotary (wheel) or nozzle atomizers. Evaporation of moisture from the droplets and formation of dry particles proceeds under controlled temperature and airflow conditions. Powder typically is discharged continuously from the drying chamber.

Typically, the present aqueous solution containing the uronic acid oligosaccharide is dried by spraying into an atmosphere with a temperature of 40 to 80° C., preferably a temperature between 50 and 65° C. It was found that this is the optimal temperature range. A lower temperature requires a spray-drying tower that is too big, making the process expensive. A higher temperature increases the risk of Maillard reactions occurring.

For spray drying the present aqueous solutions, different nozzles may be used, preferably a rotary atomizer or a two fluid nozzle is used. Preferably a two fluid nozzle is used in a co-current mode. The two fluid nozzle is preferably located in the centre of the chamber roof. The atomization is typically created by compressed air at a pressure of 0.5-2.0 bar. The feed and atomizing gas are passed separately to the nozzle head where the atomization takes places. This provides an optimal particle size distribution, of the powder.

Other Processing Steps

Prior to the spray drying process in the present process for making powder compositions, the uronic acid oligosaccharide containing solution may be treated to yield an aqueous solution suitable for spray drying. Uronic acid oligosaccharide containing solutions are preferably prepared by hydrolysis, preferably enzymatic hydrolysis, of uronic acid polymers (e.g. DP>1000). This generally yields an uronic acid containing solution with a dry matter content below 30 wt. % based on total weight of the solution. It is disadvantageous and costly to spray dry solutions having a low dry matter content. Hence, prior to the spray-drying step, preferably an uronic acid oligosaccharide containing solution is subjected to a processing step for increasing dry matter content, preferably reversed osmosis and/or evaporation. This processing step preferably yields an high uronic acid oligosaccharide solution as described above. To prevent Maillard reactions from occurring, the processes are preferably conducted at a temperature below 60° C.

In a further preferred embodiment, the present invention provides a process for the production of a powdered product from an aqueous solution comprising step a: a mixing step comprising admixing a uronic acid oligosaccharide containing powder, water, protein and carbohydrate to form an aqueous solution containing between 0.1 and 5 wt. % oligosaccharides based on dry weight of the aqueous solution;

step b: a heating step comprising heating the aqueous solution obtained in the mixing step to a temperature between 50 and 90° C.;

step c: a second mixing step wherein fat is mixed with the aqueous solution that has been subjected to heat in the heating step, to yield a fat containing aqueous solution; and step d: a spray drying step wherein the fat containing aqueous solution is spray dried to form a powder composition with an oligosaccharide content of between 0.1 and 5 wt. % uronic acid oligosaccharide based on total dry weight of the composition.

FIG. 1 show a schematic representation of a preferred embodiment of the present process.

Preferably, the uronic acid oligosaccharide containing powder used in mixing step a. is the uronic acid oligosaccharide containing powder according to the present invention, e.g. obtained or obtainable by spray drying the present high uronic acid oligosaccharide solution. Preferably the heating step b. comprises heating the aqueous solution obtained in the mixing step to a temperature between 50 and 90° C. for a time interval of at least between 5 seconds. Preferably the heating step b. is less than 5 minutes. The short heating time provides a heated and pasteurized product with minimal Maillard reaction products.

EXAMPLES

Example 1

Spray Drying an Aqueous Solution Containing Uronic Acid Oligosaccharide

An aqueous solution containing about 25 wt. % uronic acid oligosaccharides prepared by lyase hydrolysis of pectin, and with an average DP of 5 and a dry matter content of 35 wt. %, is concentrated by reversed osmosis, to form a concentrated aqueous solution with a dry matter content of 45 wt. %.

The aqueous solution was spray dried on a spray dryer (toll dryer), at about 150 bar nozzle pressure; Tin=192° C., Tout=92° C.; product temperature in =72° C. The yielding powder was further dried on a fluidized bed (75° C.). The average particle diameter of the resulting powder was 53.7 micrometer (μm), with about 10% of the particles have a particle size diameter below 18 μm and about 10% of the particles have a particle size diameter above 97.2 μm. The powder has an acceptable color, indicating minimal occurrence of Maillard reaction products.

Example 2

Spray Drying an Aqueous Solution Containing Uronic Acid Oligosaccharide

An aqueous solution is prepared that contains: 1 gram polygalacturonic acid (lyase digested pectin with average DP of 6) per 100 grams dry weight; 12 grams protein (casein and whey protein) per 100 grams dry weight; and 60 grams lactose per 100 grams dry weight; 6 grams galactooligosaccharides per 100 grams dry weight, and a dry matter content of 50% based on weight.

The aqueous solution was spray dried on a spray dryer (toll dryer), at about 150 bar nozzle pressure; Tin=192° C., Tout=92° C.; product temperature in =72° C. The yielding powder was further dried on a fluidized bed (75° C.). The average particle diameter of the resulting powder was 53.7 micrometer (μm), with about 10% of the particles have a particle size diameter below 18 μm and about 10% of the particles have a particle size diameter above 97.2 μm. The powder has an acceptable color, indicating minimal occurrence of Maillard reaction products.

The invention claimed:

1. A process for the production of a powdered product from an aqueous solution comprising:
   a. admixing powder comprising uronic acid oligosaccharide with a degree of polymerization (DP) of 2 to 250, water, protein and carbohydrate to form an aqueous solution comprising between 0.1 and 5 wt. % uronic acid oligosaccharides based on dry weight of the aqueous solution;
   b. heating the aqueous solution obtained in (a) to a temperature between 50 and 90° C.;
   c. mixing fat with the aqueous solution of (b), to yield a fat containing aqueous solution; and
   d. spray drying the fat containing aqueous solution to form a powder composition with an oligosaccharide content of between 0.1 and 5 wt. % uronic acid oligosaccharide based on total dry weight of the composition, wherein the spray dried product is substantially free of Maillard reaction products.

2. The process according to claim 1, wherein the aqueous solution comprises between 2 and 25 grams protein per 100 grams dry weight, between 20 and 80 grams digestible carbohydrate per 100 grams dry weight, and between 5 and 40 grams fat per 100 grams dry weight.

3. A powder composition obtainable by:
   a. admixing powder comprising uronic acid oligosaccharide with a degree of polymerization (DP) of 2 to 250, water, protein and carbohydrate to form an aqueous solution comprising between 0.1 and 5 wt. % uronic acid oligosaccharides based on dry weight of the aqueous solution;
   b. heating the aqueous solution obtained in (a) to a temperature between 50 and 90° C.;
   c. mixing fat with the aqueous solution of (b), to yield a fat containing aqueous solution; and
   d. spray drying the fat containing aqueous solution to form a powder composition with an oligosaccharide content of between 0.1 and 5 wt. % uronic acid oligosaccharide based on total dry weight of the composition, wherein the powder composition is substantially free of Maillard reaction products.

4. The powder composition according to claim 3, wherein the average particle size is between 20 μm and 100 μm.

5. The powder composition according to claim 3, wherein the uronic acid oligosaccharide is galacturonic oligosaccharide.

6. The powder according to claim 3, comprising, per 100 grams powder, between 2 and 20 grams protein, between 20 and 75 grains carbohydrate, between 10 and 40 grams fat and between 0.1 and 5 grams of the uronic acid oligosaccharide with a DP of 2 to 50, wherein the uronic acid powder particles comprise a mixture of said protein, carbohydrate and fat.

7. The process according to claim 1, wherein the uronic acid oligosaccharide is galacturonic acid oligosaccharide with a DP between 2 and 50.

* * * * *